(12) United States Patent
Chen et al.

(10) Patent No.: US 12,122,970 B2
(45) Date of Patent: Oct. 22, 2024

(54) PRODUCTION CHEMICALS AND METHODS OF SELECTING THE PRODUCTION CHEMICALS BASED ON HANSEN SOLUBILITY PARAMETERS

(71) Applicant: Cameron International Corporation, Houston, TX (US)

(72) Inventors: Yiyan Chen, Sugar Land, TX (US); Changping Sui, The Woodlands, TX (US)

(73) Assignee: CAMERON INTERNATIONAL CORPORATION, Houston, TX (US)

( * ) Notice: Subject to any disclaimer, the term of this patent is extended or adjusted under 35 U.S.C. 154(b) by 164 days.

(21) Appl. No.: 17/649,951

(22) Filed: Feb. 4, 2022

(65) Prior Publication Data

US 2023/0250350 A1   Aug. 10, 2023

(51) Int. Cl.
  *C10L 10/00* (2006.01)
  *C10L 10/04* (2006.01)
  *G16C 20/30* (2019.01)

(52) U.S. Cl.
  CPC ............. *C10L 10/04* (2013.01); *G16C 20/30* (2019.02); *C10L 2290/58* (2013.01); *C10L 2290/60* (2013.01)

(58) Field of Classification Search
  CPC .. C10L 10/04; C10L 2290/58; C10L 2290/60; G16C 20/30
  See application file for complete search history.

(56) References Cited

U.S. PATENT DOCUMENTS

| 9,458,389 | B1 | 10/2016 | Schabron et al. |
| 2011/0172924 | A1 | 7/2011 | Hughes et al. |
| 2016/0355738 | A1 | 12/2016 | Schlosberg et al. |

FOREIGN PATENT DOCUMENTS

| WO | 2020228990 A1 | 11/2020 | |
| WO | WO-2020228991 A1 * | 11/2020 | ............. C10G 1/008 |

OTHER PUBLICATIONS

Hansen, (2007) Hansen Solubility Parameters: A User's Handbook, Second Edition, Chapters, 1, 2, 4, 5 and 9 (136 pages).
International Search Report and Written Opinion issued the PCT Application No. PCT/US2023/011824 dated May 15, 2023, 9 pages.

* cited by examiner

*Primary Examiner* — Taiwo Oladapo
(74) *Attorney, Agent, or Firm* — Jeffrey D. Frantz

(57) ABSTRACT

Production chemicals and methods of selecting the production chemicals based on Hansen Solubility Parameters (HSP) are disclosed. The production chemicals selected by the methods mitigate or reduce one or more issues or problems associated with oil and gas productions and transportations. The methods measure HSP values for the production chemicals and/or crude oil and select at least one production chemical for at least one application on the crude oil based on the HSP values of the production chemicals and the crude oil.

7 Claims, 7 Drawing Sheets

PRODUCTION CHEMICALS AND METHODS OF SELECTING THE PRODUCTION CHEMICALS BASED ON HANSEN SOLUBILITY PARAMETERS

FIELD OF THE DISCLOSURE

One or more production chemicals (hereinafter "production chemicals") and methods of selecting the production chemicals based on Hansen Solubility Parameters (hereinafter "HSP") are disclosed herein. The selected production chemicals are usable to mitigate or reduce one or more issues or problems associated with oil and gas productions and/or transportations. The methods disclosed herein measure, calculate, and utilize HSP information associated with the production chemicals and at least one crude oil to identify the selected production chemicals for application to the at least one crude oil. The methods disclosed herein may select at least one production chemical for one or more applications to crude oil based on the HSP information associated with the at least one production chemical and/or the crude oil.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

In one or more embodiments, a method for selecting one or more production chemicals for a crude oil application is provided. The method comprises measuring Hansen Solubility Parameters (HSP) values for a plurality of production chemicals to provide HSP information of the plurality of production chemicals and measuring HSP values for crude oils to be treated by the plurality of production chemicals. Further, the method comprises comparing the HSP information of the plurality of production chemicals to HSP information of a target crude oil and selecting at least one production chemical from the plurality of production chemicals based on the compared HSP information of the plurality of production chemicals and the target crude oil.

In an embodiment, the selected at least one production chemical has a HSP value located within the Hansen space associated with the target crude oil.

In an embodiment, the method further comprises applying the selected at least one production chemical to the target crude oil, a production stream associated with the target crude oil, equipment associated with the target crude oil, or a combination thereof.

In an embodiment, the HSP values of the production chemicals comprise at least three values for each production chemical defined as strengths of dispersion interaction $\delta D$, polar interaction $\delta P$, and hydrogen bonding $\delta H$.

In an embodiment, the HSP information of the target crude oil comprises at least four values for the target crude oil defined as strengths of dispersion interaction $\delta D$, polar interaction $\delta P$, hydrogen bonding $\delta H$, and R0.

In an embodiment, the method further comprises measuring the HSP values of the target crude oil by utilizing at least one of chromatography filter paper and with visible or UV light before comparing the HSP information of the plurality of production chemicals to the HSP information of the target crude oil.

In an embodiment, the selected at least one production chemical is at least one chemical selected from the group consisting of biocides, corrosion inhibitors, de-foamers, emulsifiers, foamers, rig washes, scale inhibitors, hydrogen sulphide scavengers, formulated emulsion breakers, paraffin inhibitors, gas hydrate inhibitor, asphaltene inhibitor, de-oilers/water clarifiers, and at least one combination thereof.

In one or more embodiments, a method comprises predicting chemical performances of one or more production chemicals on a crude oil by correlating Hansen Solubility Parameters (HSP) values between the one or more production chemicals and the crude oil and selecting at least one production chemical for treating the crude oil based on the predicted chemical performances.

In an embodiment, the method further comprises applying the selected at least one production chemical to the crude oil, a production stream associated with the crude oil, equipment associated with the crude oil, or a combination thereof.

In an embodiment, the method further comprises inhibiting and/or treating one of corrosion, emulsion(s), gas hydrates, scale, bacteria, foam, wax, paraffin, asphaltenes, grease build-up, heterogeneous material build-up, or hydrogen sulfide within the crude oil by applying the selected at least one production chemical to the crude oil.

In an embodiment, the HSP values of the one or more production chemicals and the crude oil comprise at least four values for each production chemical and at least four values for the crude oil, wherein the at least four values are defined as strengths of dispersion interaction $\delta D$, polar interaction $\delta P$, hydrogen bonding $\delta h$, and R0.

In an embodiment, the method further comprises measuring the HSP values of the one or more production chemicals and/or the crude oil before the HSP values are correlated to predict the chemical performances of the one or more production chemicals on the crude oil.

In an embodiment, the HSP values of the selected at least one production chemical are located on a 3D graph within a radius of a 3D sphere, and the HSP values of the crude oil are a center of the 3D sphere.

In an embodiment, the selected at least one production chemical is at least one chemical selected from the group consisting of biocides, corrosion inhibitors, de-foamers, emulsifiers, foamers, rig washes, scale inhibitors, hydrogen sulphide scavengers, formulated emulsion breakers, paraffin inhibitors, gas hydrate inhibitor, asphaltene inhibitor, de-oilers/water clarifiers, and at least one combination thereof.

In one or more embodiments, a method for selecting one or more production chemicals for a crude oil application is provided. The method comprises measuring Hansen Solubility Parameters (HSP) values of a crude oil and selecting at least one production chemical for the crude oil application based on HSP values of the at least one production chemical and the measured HSP values of the crude oil.

In an embodiment, the method further comprises measuring the HSP values of the at least one production chemical before selecting the at least one production chemical.

In an embodiment, the method further comprises applying the selected at least one production chemical to the crude oil, a production stream associated with the crude oil, equipment associated with the crude oil, or a combination thereof.

In an embodiment, the HSP values of the at least one production chemical and the measure HSP values of the crude oil comprise at least four values for the at least one production chemical and the crude oil, wherein the at least four values are defined as strengths of dispersion interaction $\delta D$, polar interaction $\delta P$, hydrogen bonding $\delta H$, and $R_0$.

In an embodiment, the selected at least one production chemical is at least one chemical selected from the group consisting of biocides, corrosion inhibitors, de-foamers, emulsifiers, foamers, rig washes, scale inhibitors, hydrogen sulphide scavengers, formulated emulsion breakers, paraffin inhibitors, gas hydrate inhibitor, asphaltene inhibitor, de-oilers/water clarifiers, and at least one combination thereof.

In an embodiment, the HSP values of the at least one production chemical are located on a graph within a radius of a 3D sphere and the measured HSP values of the crude oil are a center of the 3D sphere.

BRIEF DESCRIPTION OF THE DRAWINGS

The present disclosure is best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion.

FIGS. 1A-1C illustrate graphs pairing plots of Hansen Solubility Parameters $\delta D$, $\delta P$, and $\delta H$, wherein FIG. 1A shows $\delta P$~$\delta D$, FIG. 1B shows $\delta H$~$\delta D$, and FIG. 1C shows $\delta H$~$\delta P$, according to one or more examples of the disclosure.

DETAILED DESCRIPTION

Figure 1A:
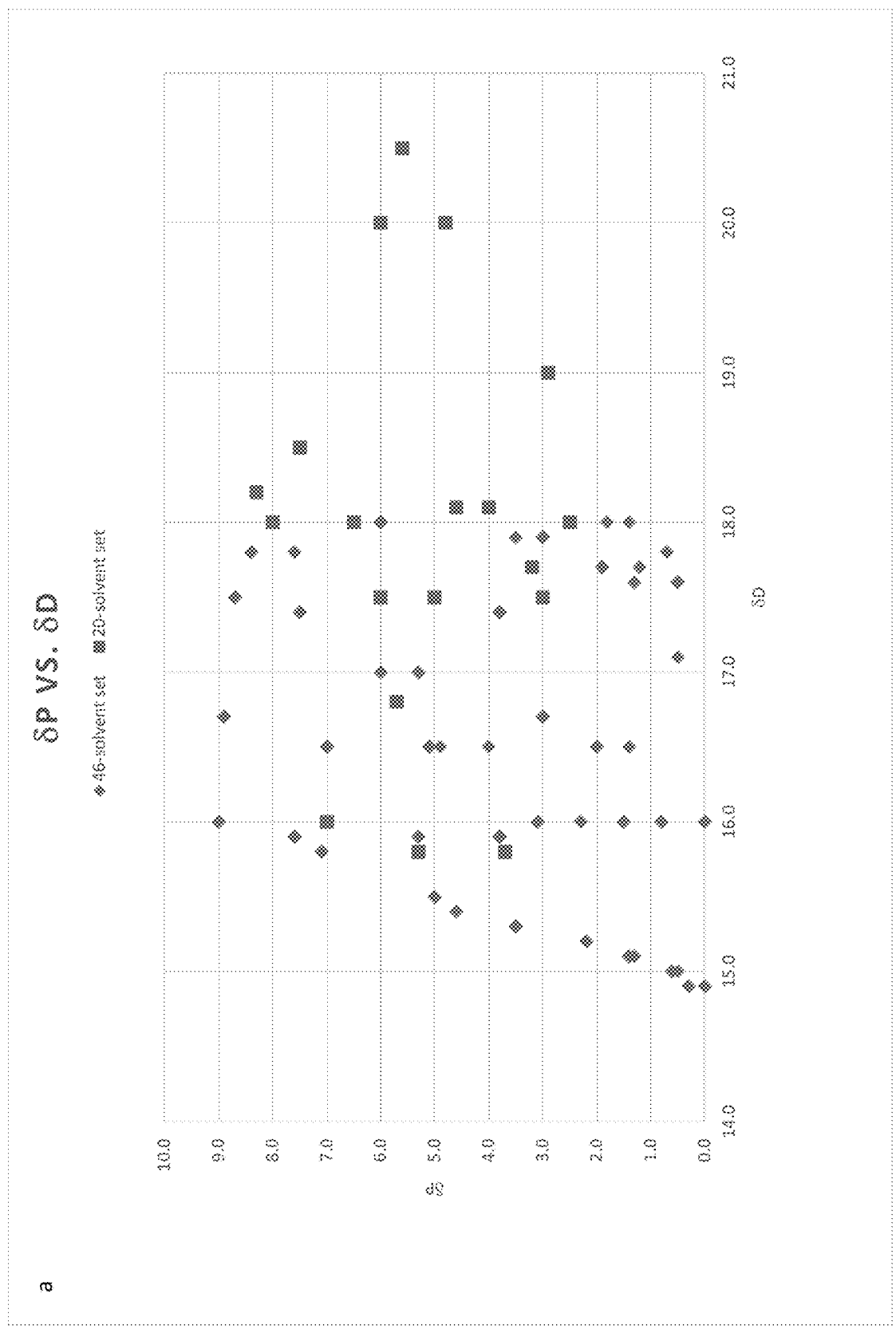

Illustrative examples of the subject matter claimed below will now be disclosed. In the interest of clarity, not all features of an actual implementation are described in this specification. It will be appreciated that in the development of any such actual implementation, numerous implementation-specific decisions may be made to achieve the developers' specific goals, such as compliance with system-related and business-related constraints, which will vary from one implementation to another. Moreover, it will be appreciated that such a development effort, even if complex and time-consuming, would be a routine undertaking for those of ordinary skill in the art having the benefit of this disclosure.

Further, as used herein, the article "a" is intended to have its ordinary meaning in the patent arts, namely "one or more." Also, the phrases "selected from the group consisting of," "chosen from," and the like include mixtures of the specified materials. Terms, such as, for example, "contains" and the like are meant to include "including at least" unless otherwise specifically noted.

Herein, the term "about" when applied to a value generally means within the tolerance range of the equipment used to produce the value, or in some examples, means plus or minus 10%, or plus or minus 5%, or plus or minus 1%, unless otherwise expressly specified. Further, herein the term "substantially" as used herein means a majority, or almost all, or all, or an amount with a range of about 51% to about 100%, for example. Moreover, examples herein are intended to be illustrative only and are presented for discussion purposes and not by way of limitation. Where a numerical limit or range is stated herein, the endpoints are included. Also, all values and subranges within a numerical limit or range are specifically included as if explicitly written out.

The present disclosure generally relates to production chemicals and methods of selecting at least one production chemical based on at least the HSP of the production chemicals. The selected production chemical is usable to mitigate or reduce one or more issues or problems associated with oil and gas productions and transportations. The methods disclosed herein may select at least one production chemical, based on the HSP, for one or more applications to a crude oil medium associated with the oil and gas productions and transportations. To effectively mitigate or reduce the one or more issues or problems associated with the oil and gas production and/or transportation, the selected production chemical(s) may function in the crude oil medium and may be compatible with the crude oil medium.

In some embodiments, the one or more crude oil applications may be associated with, for example, an organic flow assurance. For example, the one or more applications may comprise, but are not limited to, at least one application selected from demulsifiers, wax inhibition, asphaltene inhibition, pour point depressant, or a combination thereof. The at least one production chemical may be at least one chemical useful in the production and/or transportation of crude oil and other petroleum products. In other embodiments, the at least one production chemical may be useful in exploration and development and during drainage of hydrocarbons from an oil or gas field. The hydrocarbons may be complex mixtures that may be in the form of crude oils, bitumen, asphalts, or a mixture thereof. In further embodiments, the at least one production chemical may be at least one chemical selected from the group consisting of corrosion inhibitor, demulsifier, gas hydrate inhibitor, scale inhibitor, biocide/bactericide, defoamer, wax/paraffin inhibitor, asphaltenes dispersant, pour point depressant, anti-agglomerant, hydrogen sulfide scavenger, and at least one combination thereof. In still further embodiments, the at least one production chemical may comprise at least one chemical selected from the group consisting of biocides, corrosion inhibitors, de-foamers, emulsifiers, foamers, rig washes, scale inhibitors, hydrogen sulphide scavengers, formulated emulsion breakers, paraffin inhibitors, de-oilers/water clarifiers, and at least one combination thereof. Although the production chemicals and methods disclosed herein are applicable to numerous crude oil applications, the present disclosure may focus on, but is not limited to, pour point depressant functionality as an application example.

In other embodiments, the production chemicals disclosed herein may comprise at least one selected from a chemical, a composition, a formulation, or the like, utilized to support and/or enhance the production, processing, and/or transportation of petroleum products and crude oils. For example, the production chemicals may include, but are not limited to, chemicals and/or compositions to inhibit one of corrosion, emulsion(s), gas hydrates, scale, bacteria, foam, wax, paraffin, asphaltenes, grease build-up, heterogeneous material build-up, hydrogen sulfide, or a combination thereof. Multiple factors may be considered before selecting the appropriate production chemical or combination of production chemicals, which may include, but are not limited to, HSP information, performance, environmental restrictions, compatibility, stability, cost, or at least one combination thereof. In some embodiments, the methods disclosed herein may select at least two different production chemicals for introduction or addition into production streams or equipment for treating the petroleum products or crude oils. The at least two different production chemicals may not be otherwise compatible to be introduced or delivered together but may be simultaneously introduced or delivered as a single production product package through the HSP relationship or compatibility of the at least two different production chemicals. For example, the methods disclosed herein may select production chemicals based on HSP information associated with the production chemicals and/or combine at least two different production chemicals into a single production product based on the HSP information. Thus, the selected production chemicals and/or the single production product may be multi-functional and/or may be usable to treat the petroleum products and crude oils and/or other fluids, such as, for example, oil-based fluids, aqueous-based fluids, or a combination thereof.

For purposes herein, an oil-based fluid may refer to any fluid which comprises a hydrocarbon. Oil-based fluids disclosed herein may include crude oil, crude oil condensate, and/or various streams which may be produced during extraction of hydrocarbons from oil and/or gas wells. Also included are refined streams including various fuel oils, diesel fuel, kerosene, gasoline, one or more combinations thereof, and/or the like. An aqueous-based fluid disclosed herein may include tap water, produced water from a reservoir, sea water, brines, one or more combinations thereof, and/or the like. Further, it is envisioned that aqueous-based fluids may include at least some water miscible compounds, such as, for example, alcohols and/or the like.

In one or more embodiments, at least one production chemical may be selected by at least one method disclosed herein for crude oil application and/or crude oil treatment. The methods disclosed herein may select the at least one production chemical based on HSP information associated with the at least one production chemical and the crude oil. However, crude oils from different fields or even different wells of a same field may have different properties, and a production chemical that may work in first situation for a first well may not work in second situation for a second well. Although there is anecdotal evidence built from experiences in selecting one or more production chemicals for at least one crude oil production function, most product chemical selections may be based on completing multiple performance tests of multiple production chemicals with a target crude oil medium. Thus, production chemical selection for a specific crude oil or the target crude oil medium often involves repeating multiple performance tests without much or any scientific or intellectual guidance.

The lack of guidance in production chemical selection may be due to lack of understanding of as to what governs production chemical performances in different crude oils. Organic flow assurance chemicals typically need to have one or more specific parts/segments of the production chemical molecule that matches or substantially matches the problematic components in the target crude oil medium. Often, the one or more specific parts/segments of the production chemical molecules may associate with or substantially associate with problematic molecules within the target crude oil medium and participate in one or more activities of the problematic molecules, such as, for example, crystallization. However, good production chemical performances may not be guaranteed with one or more specific parts/segments of the production chemical molecules. For example, the same matching or substantially matching production chemical(s) or product may work effectively in a first crude oil but may not work effectively in a second crude oil. In another example, production chemical(s) or product that have seemingly the same or substantially the same chemistry and composition may or may not work effectively for treating the same crude oil.

As disclosed herein, the performance effectiveness of a production chemical(s) or product may be based on, associated with, related to, and/or indicative of a conformational structure of the production chemical(s) or product in a crude oil environment (hereinafter "the crude oil"). In embodiments disclosed herein, the production chemical in the crude oil must allow the functional segments of the production chemical molecules to be extended or extendible to associate with the problematic components in the crude oil to participate in the crystallization to interfere its process. If it is not the case, the production chemical molecule may contract tightly in a conformation which may provide no opportunity for the production chemical to co-crystallize with the problematic components in the crude oil. According to the "like-dissolve-like" theory, the functioning production chemical or at least one production chemical selected by the methods disclosed herein must have similar or substantially similar solubility properties as the crude oil for said production chemical to be soluble and thus effectively extended or extendible into the crude oil.

An effective production chemical or product, selected by the methods disclosed herein, may have at least one solubility property that matches or at least partially or substantially matches at least one solubility property of a target crude oil. The at least one solubility property of the crude oil is a function of a composition of the crude oil which may vary greatly across portions of the crude oil. Multiple issues have been associated with known processes to predict the solubility property of crude oil based on the composition of the crude oil. These issues include: availability of the composition data, which requires a costly Saturate, Aromatic, Resin and Asphaltene (hereinafter "SARA") analysis which is time consuming and often includes accuracy errors for the minor components of the crude oil which substantially influence the solubility property (e.g. surface-active species); inclusion of production related by-products which may be an integral part of the produced fluid but would be removed before SARA analysis (e.g. formation brine, stimulation fluid, and emulsions formed with any aqueous components); and lack of true validated model to calculate the solubility properties.

In embodiments disclosed herein, the present methods obtain, determine, calculate, and/or predict solubility properties of the crude oil without requiring difficult and sometimes inaccurate crude oil composition information. The methods disclosed herein may utilize HSP information to characterize, obtain, determine, and/or predict at least one solubility property of at least one bulk sample, at least one production chemical, at least one crude oil, or a combination thereof. According to the HSP theory, the solubility property of any substance is defined by a set of values in a 3-D solubility space which may also be referred to as the so-called "Hansen space". The set of values comprise three values that are defined as strengths of dispersion interaction $\delta D$, polar interaction $\delta P$, and hydrogen bonding $\delta H$. Each substance (i.e., a first substance) possesses, in a 3D graphical illustration, a 3D sphere in the 3D solubility or Hansen space with the $\delta D$, $\delta P$, and $\delta H$ being the center of the 3D sphere and the solubilizing power of each substance being the radius of the 3D sphere. If the δD, δP, and δH values of second substance are located inside the 3D sphere of the first substance, then second substance is soluble in the first substance, or vice versa; otherwise, the second substance is insoluble in the first substance. If the two substances (i.e., the first and second substances) are closer in the solubility or Hansen space, the two substances are more soluble in each other than when the two substances are farther apart in the solubility or Hansen space.

In one or more embodiments, the methods disclosed herein may determine, calculate, predict, collect, and/or obtain the HSP values or information (i.e., at least the δD, δP, and δH values) of the crude oil to be treated and/or the production chemical (which may already comprise the parts/segments that are similar to or substantially similar to the problematic components in the crude oil). Further, the present method may compare the HSP information of the production chemical to the HSP values or information of the crude oil to be treated and/or determine, obtain, and/or predict effectiveness of the production chemical for treating the crude oil based on the compared HSP values or information of the production chemical and the crude oil.

In some embodiments, the methods disclosed herein may measure or collect HSP (i.e., δD, δP, δH, and $R_0$ (solubility sphere radius)) values for one or more production chemicals and a crude oil to generate, create, and/or obtain HSP values or information for the production chemicals and crude oil. Further, the present methods may select at least one production chemical for application and treatment of the crude oil based on a comparison of the HSP values or information of the production chemicals and crude oil. Still further, the present methods may treat the crude oil with the selected production chemical, apply the selected production chemical to the crude oil, and/or add, deliver, or introduce the selected production chemical into the crude oil and/or a production stream or equipment associated with the crude oil.

In other embodiments disclosed herein, the present methods may measure HSP properties (i.e., at least δD, δP, and δH values) for crude oil and one or more production chemicals and correlate performances of at least one production chemical on the crude oil based on the measured HSP properties. Further, the present methods may propose, generate, predict, or formulate at least one production chemical selection process for a crude oil treatment or crude oil application based on the correlated performances or predicted performances of the at least one production chemical on the crude oil. Still further, the present methods may select at least one production chemical for the crude oil treatment or crude oil application based on the selection process and/or treat the crude oil with the selected production chemical(s) by adding, introducing, or delivering the selected production chemical(s) into the crude oil or a production stream or equipment associated with the crude oil.

In one or more embodiments, the production chemicals and/or the methods disclosed herein may comprise one or more solvents or solvent packages (hereinafter "solvent packages") that are designed with broad coverages with respect to δD, δP, and δH values. As used herein, the term "solvent" refers to the liquid in which a solute is dissolved and/or dispersed and encompasses mixtures of liquids unless otherwise specified. The HSP values or information comprising δD, δP, δH, and $R_0$ values (collectively referred to hereinafter as "HSP information") of a substance may be obtainable by testing the substance with a plurality of solvents to determine if the substance is soluble in each solvent of the plurality of solvents. In some embodiments, the substance disclosed herein may be or may comprise the at least one production chemical or a combination of at least two production chemicals. The plurality of solvents tested may include a series or plurality of solvents with known HSP information. The obtained results of the solubility tests with the plurality of solvents may be inputted into Hansen Solubility Parameters in Practice (hereinafter "HSPiP") software available at https://www.hansen-solubility.com/HSPiP and analyzed by the HSPiP software in accordance with the user manual or instructions also available at https://www.hansen-solubility.com/HSPiP. The HSP information for common solvents, such as, of example, acetone, methanol, dimethyl sulfoxide (DMSO), toluene, cyclohexane, and like solvents are well known and readily available, for example, in the commercially available HSPiP database accessible via the HSPiP software.

As a result of the analysis via the HSPiP software, best fitting HSP values of the substance (i.e., δD, δP, δH, and $R_0$ values) are calculated that maximize the fit of soluble and insoluble results by placing the soluble solvent(s), which is defined or definable by the δD, δP, and δH values of the solvent in the 3D solubility space or Hansen space inside the defined soluble sphere and the insoluble solvent(s) outside the soluble sphere. To accurately obtain the HSP information, the solvents that may be selected have good coverage of the 3-D solubility space or Hansen space and reasonable soluble and insoluble spread when dissolving the substance. It may not always be possible to select pure solvents to cover the whole solubility or Hansen space of the desired solvent package. Thus, a mixed solvent system is designed or designable by the production chemicals and the methods disclosed herein to meet the good coverage requirement for the solubility or Hansen space. Table 1 lists a first set of solvent packages that covers the solubility or Hansen space. In some embodiments, the first set of solvent packages may comprise, but is not limited to, solvent packages that are not very high or lower in at least one of polar interaction and H-bonding than other sets of solvent packages disclosed herein. In an embodiment, the first set of solvent packages may comprise, but is not limited to, forty-six (46) solvent packages that may cover a less polarity and H-bonding solubility or Hansen space. In other embodiments, the first set of solvent packages may comprise more or less than about forty-six (46) solvent packages.

TABLE 1

| | Calculated HSP | | | solvent 1 | | | solvent 2 | | | solvent 3 | | |
|---|---|---|---|---|---|---|---|---|---|---|---|---|
| ID | δD | δP | δH | name | vol % | wt % | Name | vol % | wt % | name | vol % | wt % |
| HSP-1 | 14.9 | 0.0 | 0.0 | Hexane | 100% | | | | | | | |
| HSP-2 | 14.9 | 0.3 | 0.8 | Hexane | 95% | 94% | 2-propanol | 5% | 6% | | | |
| HSP-3 | 15.0 | 0.5 | 0.4 | Hexane | 94% | 93% | MEK[a] | 5% | 6% | 1-butanol | 1% | 0.65% |
| HSP-4 | 15.0 | 0.6 | 1.7 | Hexane | 89% | 87% | 1-butanol | 11% | 13% | | | |
| HSP-5 | 15.1 | 1.3 | 3.5 | Hexane | 78% | 74% | 1-butanol | 22% | 26% | | | |
| HSP-6 | 15.1 | 1.4 | 0.8 | Hexane | 84% | 81% | MEK | 16% | 19% | | | |

TABLE 1-continued

| | Calculated HSP | | | solvent 1 | | | solvent 2 | | | solvent 3 | | |
|---|---|---|---|---|---|---|---|---|---|---|---|---|
| ID | δD | δP | δH | name | vol % | wt % | Name | vol % | wt % | name | vol % | wt % |
| HSP-7 | 15.2 | 2.2 | 1.2 | Hexane | 76% | 72% | MEK | 24% | 28% | | | |
| HSP-8 | 15.3 | 3.5 | 2.0 | Hexane | 61% | 56% | MEK | 39% | 44% | | | |
| HSP-9 | 15.4 | 4.6 | 5.0 | Hexane | 49% | 44% | MEK | 34% | 37% | ethanol | 17% | 18% |
| HSP-10 | 15.5 | 5.0 | 2.8 | Hexane | 45% | 40% | MEK | 55% | 60% | | | |
| HSP-11 | 15.8 | 7.1 | 4.0 | Hexane | 21% | 18% | MEK | 79% | 82% | | | |
| HSP-12 | 15.9 | 3.8 | 2.3 | Heptane | 48% | 44% | Toluene | 12% | 13% | MEK | 40% | 43% |
| HSP-13 | 15.9 | 5.3 | 3.0 | Heptane | 41% | 37% | cyclo-hexanone | 10% | 10% | MEK | 49% | 53% |
| HSP-14 | 15.9 | 7.6 | 4.3 | Heptane | 16% | 14% | MEK | 84% | 86% | | | |
| HSP-15 | 16.0 | 0.0 | 0.1 | Hexane | 16% | 15% | Heptane | 33% | 31% | Cyclo-hexane | 51% | 54% |
| HSP-16 | 16.0 | 0.8 | 0.5 | Heptane | 60% | 56% | cyclo-hexane | 31% | 33% | cyclo-hexanone | 9% | 12% |
| HSP-17 | 16.0 | 1.5 | 0.9 | Hexane | 35% | 31% | cyclo-hexane | 49% | 51% | MEK | 16% | 17% |
| HSP-18 | 16.0 | 2.3 | 1.3 | Heptane | 40% | 37% | cyclo-hexane | 35% | 36% | MEK | 25% | 27% |
| HSP-19 | 16.0 | 3.1 | 3.0 | Hexane | 55% | 47% | THF | 25% | 29% | cyclo-hexanone | 20% | 24% |
| HSP-20 | 16.0 | 9.0 | 5.1 | MEK | 100% | 100% | | | | | | |
| HSP-21 | 16.5 | 1.4 | 1.0 | cyclo-hexane | 75% | 76% | MEK | 16% | 17% | Hexane | 9% | 8% |
| HSP-22 | 16.5 | 2.0 | 3.0 | Toluene | 44% | 47% | Hexane | 36% | 29% | DEGMBE[b] | 20% | 24% |
| HSP-23 | 16.5 | 4.0 | 3.0 | Heptane | 50% | 42% | cyclo-hexanone | 45% | 52% | Cyclo-hexanol | 5% | 6% |
| HSP-24 | 16.5 | 4.9 | 3.0 | cyclo-hexanone | 53% | 61% | Hexane | 44% | 35% | DMF[c] | 3% | 3% |
| HSP-25 | 16.5 | 5.1 | 4.0 | cyclo-hexanone | 51% | 57% | Hexane | 35% | 27% | PGMMEA[d] | 14% | 16% |
| HSP-26 | 16.5 | 7.0 | 5.0 | MEK | 70% | 69% | Ethyle benzene | 25% | 26% | Propylene glycol | 5% | 5% |
| HSP-27 | 16.7 | 3.0 | 4.0 | d-Limonene | 69% | 71% | MEK | 20% | 20% | Hexane | 11% | 9% |
| HSP-28 | 16.7 | 8.9 | 6.1 | MEK | 58% | 54% | Cyclo-hexanone | 36% | 39% | Propylene glycol | 6% | 7% |
| HSP-29 | 17.0 | 5.3 | 3.2 | cyclo-hexanone | 41% | 46% | Cyclo-hexane | 38% | 35% | MEK | 21% | 20% |
| HSP-30 | 17.0 | 6.0 | 6.0 | cyclo-hexanone | 50% | 55% | Cyclo-hexane | 35% | 31% | Methanol | 15% | 14% |
| HSP-31 | 17.1 | 0.5 | 1.8 | Cyclo-hexane | 65% | 62% | Xylene | 29% | 31% | Cyclo-hexanol | 6% | 7% |
| HSP-32 | 17.4 | 3.8 | 2.6 | Ethyl benzene | 17% | 17% | cyclo-hexane | 39% | 35% | cyclo-hexanone | 44% | 48% |
| HSP-33 | 17.4 | 7.5 | 4.6 | cyclo-hexane | 11% | 9% | cyclohexanone | 89% | 91% | | | |
| HSP-34 | 17.5 | 8.7 | 5.3 | cyclo-hexanone | 79% | 81% | MEK | 18% | 16% | DMF | 3% | 3% |
| HSP-35 | 17.6 | 0.5 | 1.1 | Ethyl benzene | 79% | 81% | cyclo-hexane | 21% | 19% | | | |
| HSP-36 | 17.6 | 1.3 | 1.6 | Ethyl benzene | 74% | 75% | cyclo-hexane | 16% | 14% | cyclo-hexanone | 10% | 11% |
| HSP-37 | 17.7 | 1.2 | 3.6 | Ethyl benzene | 82% | 80% | Cyclohexanol | 18% | 20% | | | |
| HSP-38 | 17.7 | 1.9 | 5.4 | Xylene | 46% | 45% | Toluene | 29% | 28% | Cyclo-hexanol | 25% | 27% |
| HSP-39 | 17.8 | 0.7 | 1.7 | Ethyl benzene | 81% | 81% | xylene | 19% | 19% | | | |
| HSP-40 | 17.8 | 7.6 | 4.8 | Toluene | 11% | 10% | cyclo-hexanone | 89% | 90% | | | |
| HSP-41 | 17.8 | 8.4 | 5.1 | cyclo-hexanone | 100% | 100% | | | | | | |
| HSP-42 | 17.9 | 3.0 | 3.0 | Toluene | 82% | 81% | cyclo-hexanone | 11% | 12% | DMF | 7% | 7% |
| HSP-43 | 17.9 | 3.5 | 2.9 | Toluene | 70% | 68% | cyclo-hexanone | 30% | 32% | | | |
| HSP-44 | 18.0 | 1.4 | 2.0 | Toluene | 100% | 100% | | | | | | |
| HSP-45 | 18.0 | 1.8 | 2.2 | Toluene | 94% | 93% | cyclohexanone | 6% | 7% | | | |
| HSP-46 | 18.0 | 6.0 | 6.0 | cyclo-hexanone | 51% | 51% | Toluene | 28% | 26% | Benzyl alcohol | 21% | 23% |

[a]MEK = methyl ethyl ketone,
[b]DEGMBE = diethylene glycol monobutyl ether,
[c]DMF = N, N-dimethyl formamide, and
[d]PGMMEA = propylene glycol monomethyl ether acetate.

With respect to organic flow assurance issues, a plurality of solvent packages of the first set of solvent packages may sufficiently distinguish soluble and insoluble behaviors for the production chemical product (comprising at least one production chemical) and the crude oil. However, there may be one or more instances when none of the solvent packages of the first set may dissolve the at least one production chemical or the at least one production chemical may dissolve in all or substantially all of the solvent packages of the first set. For those one or more instances, a second set of solvent packages may be utilized wherein a plurality of solvent packages of the second set may have, but are not limited to, at least one of higher polar interaction and/or higher H-bonding than the solvent packages of the first set. In an embodiment, Table 2 lists the solvent packages of the second set that comprise, but are not limited to, twenty (20) solvent packages that may cover more polarity and/or higher H-bonding solubility space than the solvent packages of the first set. In some embodiments, the second set of solvent packages may comprise more or less than about twenty (20) solvent packages.

more crude oils to be treated by the present production chemicals. It is well known that crude oils vary from reservoir to reservoir. Sometimes, a production process may also create variations in a single crude oil (e.g., emulsion creation). While it is not easy to construct the crude oil solubility properties from components of the crude oil, one or more HSP experiments may measure bulk oil solubility properties of the one or more crude oils.

Figure 2:
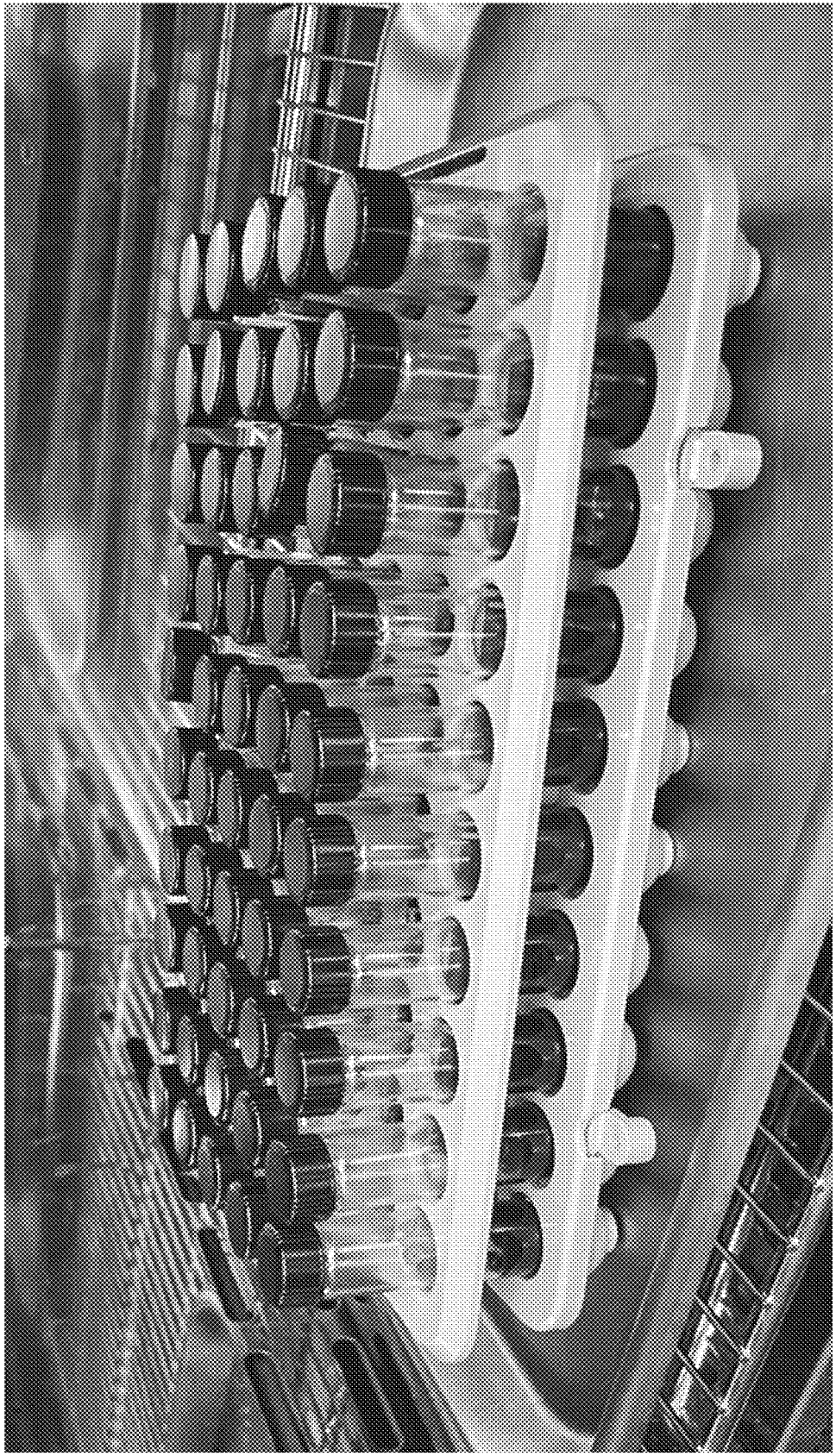
FIG. 2 illustrates crude oil in a solvent package within an oven, according to one or more examples of the disclosure.

During the one or more HSP experiments disclosed herein, a crude oil sample is warmed in an oven at about 65° C. to allow any wax to melt and is well mixed to obtain a homogeneous mixture. The oil is then weighed warm into small individual vials and a single solvent package of the first set of solvent packages is added to each individual vial such that about 20 wt % crude oil mixture is present or provided within each individual vial. The oil is kept in the oven at about 65° C. and shaken periodically to make homogeneous samples as shown in FIG. 2. Due to most crude oils being dark in color, it may be difficult to decide or determine if any phase separations are located in the about 20 wt % crude oil mixtures. In one or more embodiments,

TABLE 2

| ID | Calculated HSP | | | solvent 1 | | | solvent 2 | | | solvent 3 | | |
|---|---|---|---|---|---|---|---|---|---|---|---|---|
| | $\delta D$ | $\delta P$ | $\delta H$ | name | vol % | wt % | name | vol % | wt % | name | vol % | wt % |
| HSP-47 | 17.5 | 5.0 | 5.0 | cyclo-hexanone | 30% | 32% | Toluene | 35% | 34% | THF | 35% | 35% |
| HSP-48 | 17.5 | 6.0 | 3.0 | cyclo-hexanone | 14% | 14% | Toluene | 65% | 58% | Aceto-nitrile | 35% | 28% |
| HSP-49 | 17.5 | 3.0 | 6.0 | Toluene | 70% | 68% | EGMBE[e] | 20% | 20% | Propylene glycol | 10% | 12% |
| HSP-50 | 18.1 | 4.6 | 3.8 | Toluene | 78% | 74% | cyclo-hexanone | 1% | 1% | DMSO[f] | 21% | 25% |
| HSP-51 | 18.5 | 7.5 | 5.0 | Toluene | 38% | 35% | cyclo-hexanone | 40% | 40% | DMSO | 22% | 25% |
| HSP-52 | 17.7 | 3.2 | 8.7 | Toluene | 48% | 45% | Cyclo-hexanol | 46% | 48% | MEG[g] | 6% | 7% |
| HSP-53 | 18.1 | 4.0 | 3.4 | Toluene | 83% | 79% | DMSO | 17% | 21% | | | |
| HSP-54 | 18.0 | 2.5 | 3.4 | Toluene | 86% | 84% | Cyclo-hexanol | 8% | 9% | DMSO | 6% | 7% |
| HSP-55 | 18.2 | 8.3 | 5.8 | Toluene | 54% | 48% | DMSO | 46% | 52% | | | |
| HSP-56 | 18.0 | 6.5 | 7.5 | Toluene | 44% | 40% | Cyclo-hexanol | 27% | 27% | DMSO | 29% | 33% |
| HSP-57 | 18.0 | 8.0 | 7.9 | Toluene | 37% | 33% | Cyclo-hexanol | 23% | 23% | DMSO | 40% | 45% |
| HSP-58 | 20.5 | 5.6 | 5.7 | Quinoline | 100% | 100% | | | | | | |
| HSP-59 | 20.0 | 4.8 | 5.0 | Quinoline | 83% | 86% | Ethyl benzene | 17% | 14% | | | |
| HSP-60 | 19.0 | 2.9 | 3.4 | Quinoline | 54% | 60% | Ethyl benzene | 46% | 40% | | | |
| HSP-61 | 20.0 | 6.0 | 6.0 | Quinoline | 81% | 83% | cyclo-hexanone | 14% | 12% | Benzyl alcohol | 5% | 5% |
| HSP-62 | 16.0 | 7.0 | 10.6 | DEGMBE | 100% | 100% | | | | | | |
| HSP-63 | 15.8 | 5.3 | 7.2 | Ethyl acetate | 100% | 100% | | | | | | |
| HSP-64 | 15.8 | 3.7 | 6.3 | n-butyl acetate | 100% | 100% | | | | | | |
| HSP-65 | 16.8 | 5.7 | 8.0 | THF | 100% | 100% | | | | | | |
| HSP-66 | 15.6 | 5.6 | 9.8 | PGMMEA | 100% | 100%[δ] | | | | | | |

[e]EGMBE = ethylene glycol monobutyl ether,
[f]DMSO = dimethyl sulfoxide, and
[g]MEG = monoethylene glycol.

Figure 1B:
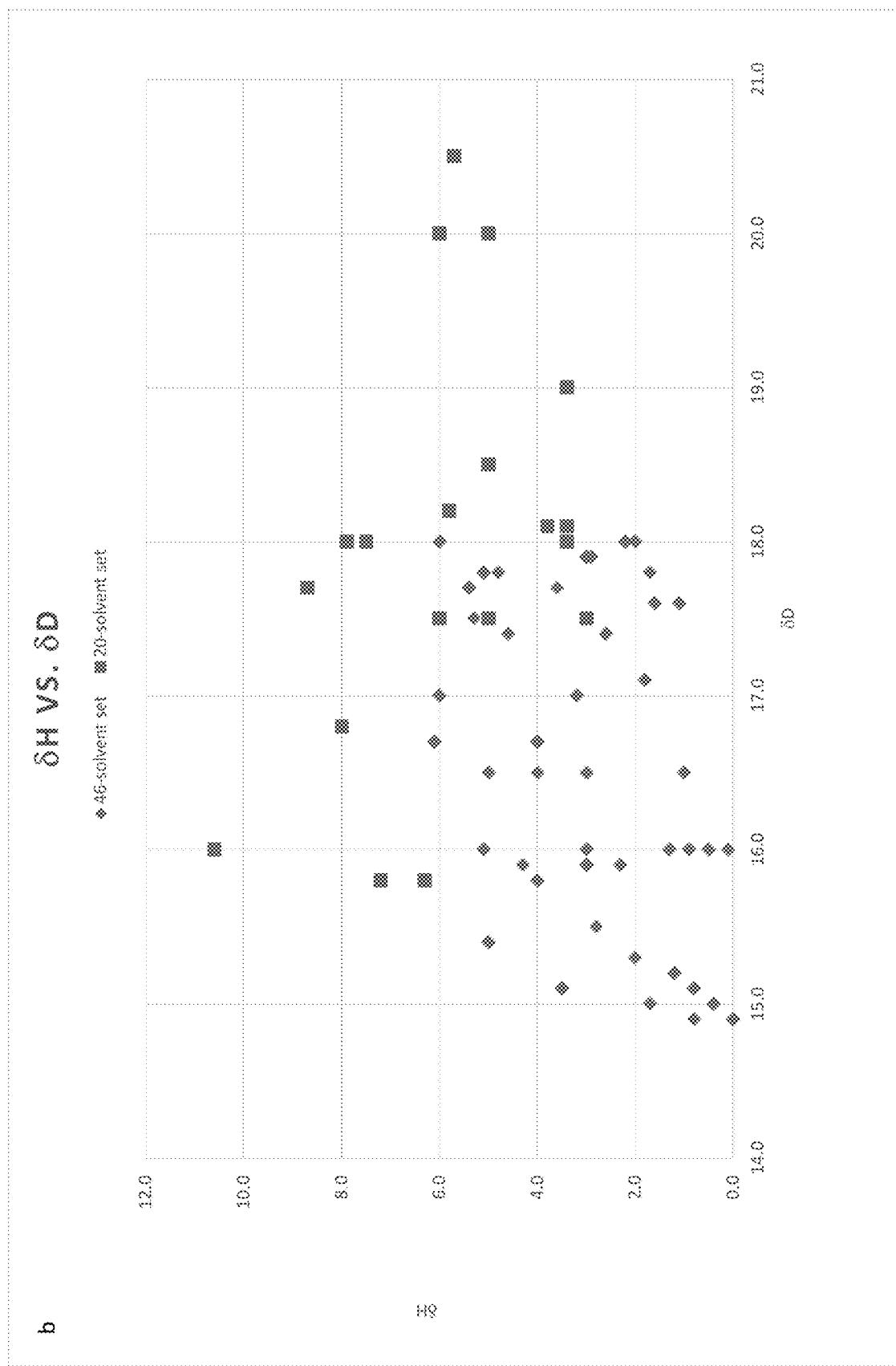
Figure 1C:
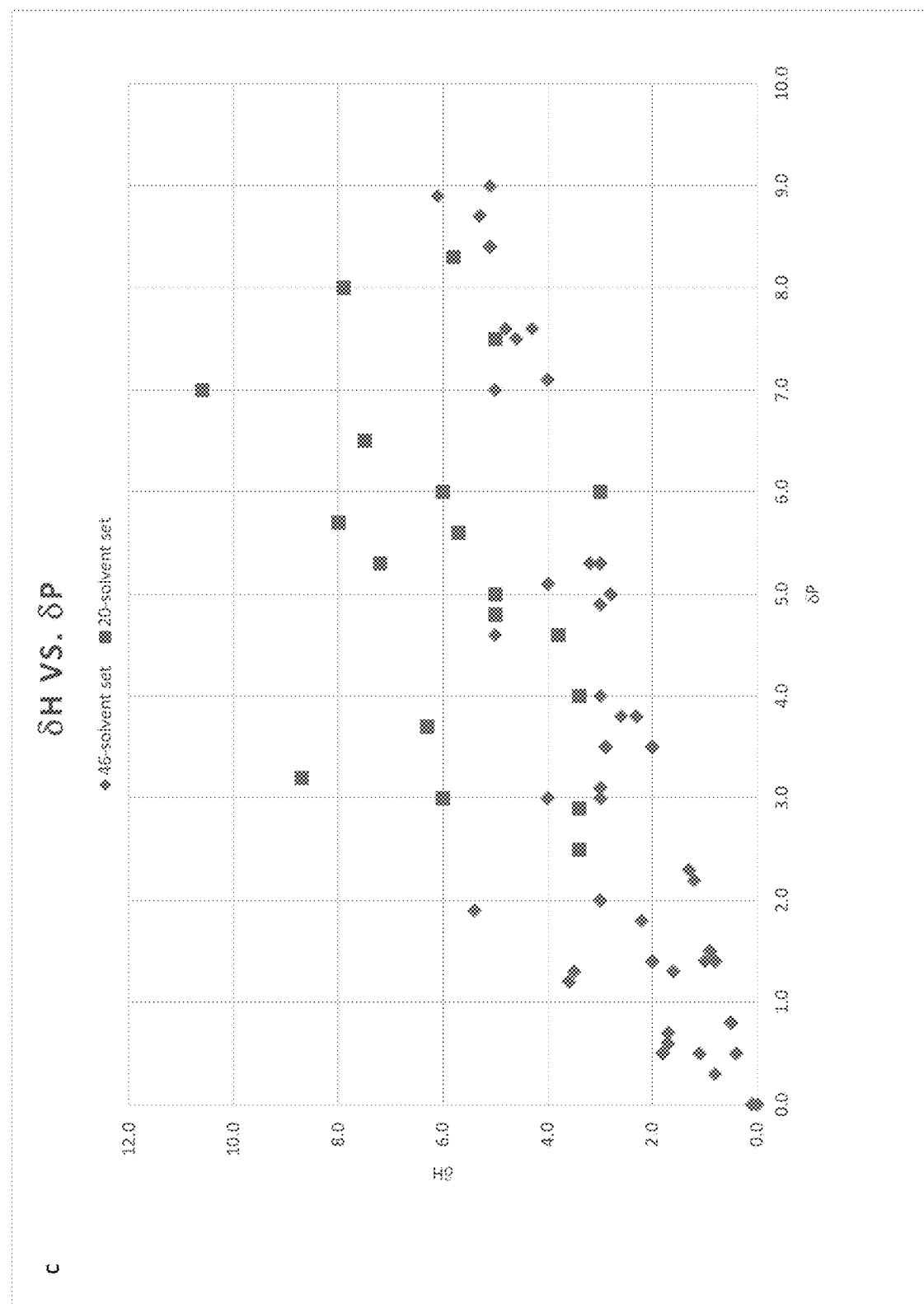

The pairing plots of $\delta D$, $\delta P$, and $\delta H$ values are given in FIGS. 1A-1C to show that the designed solvents disclosed herein cover the broad space of the HSP or Hansen space. Pairing plots of $\delta P \sim \delta D$, $\delta H \sim \delta D$, and $\delta H \sim \delta P$ are illustrated in FIGS. 1A-1C, respectively.

In one or more embodiments, the methods disclosed herein may measure, obtain, calculate, collect, and/or predict HSP information (i.e., $\delta D$, $\delta P$, $\delta H$, and $R_0$ values) for one or more crude oils. The methods disclosed herein may utilize one or more chromatography principles to determine, decide and/or conclude if the crude oil is dissolved or dissolvable in one or more solvent packages of the first set of solvent packages.

Figure 3:
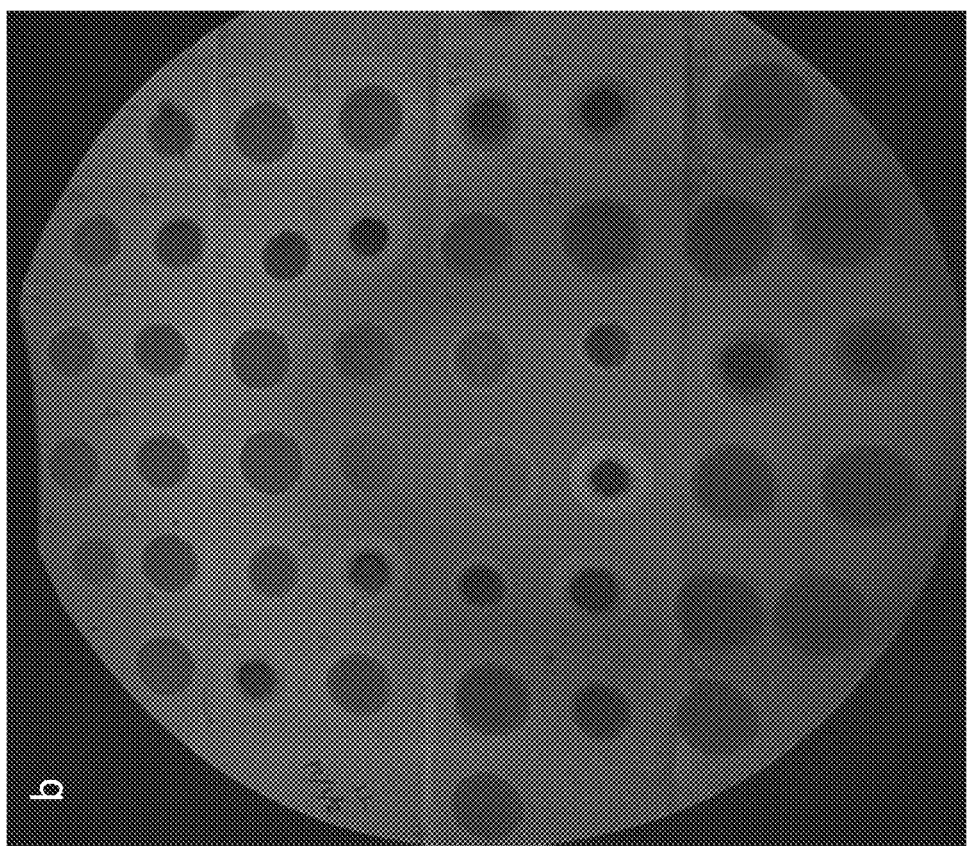
FIG. 3 illustrates a paper chromatography method to identify solubility of crude oil in solvents under, according to one or more examples of the disclosure, wherein a) is in visible light and b) is in UV light.
Figure 3:
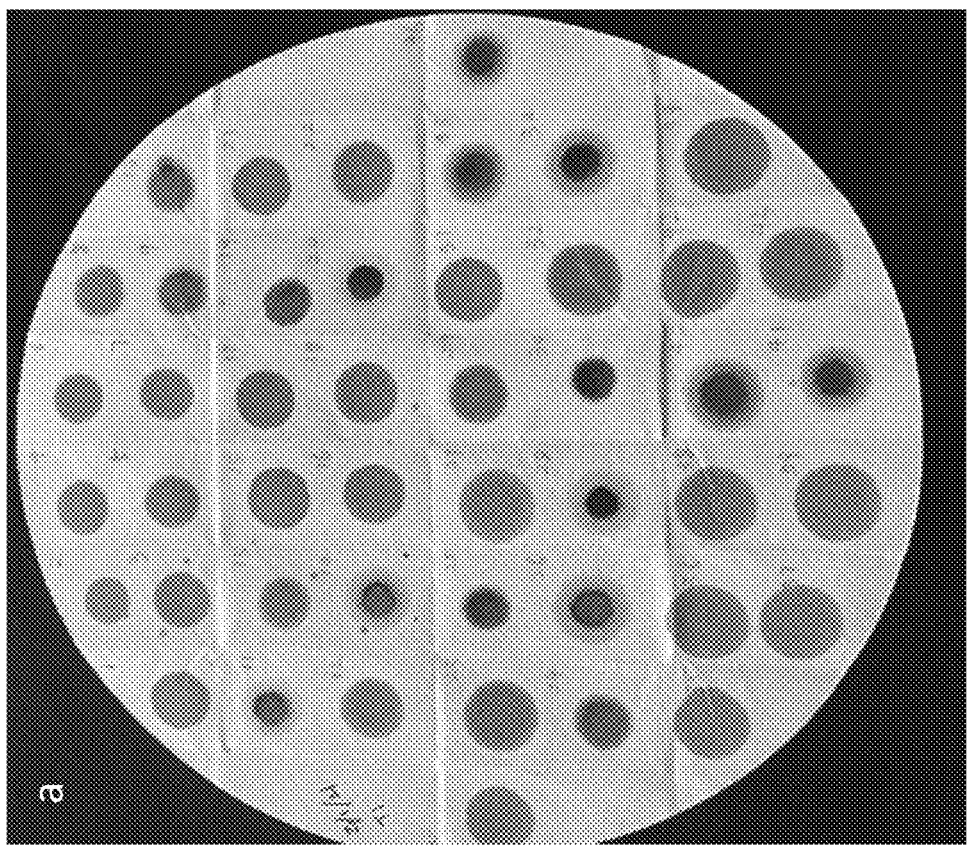

Utilizing the chromatography principles, a small amount of the crude oil mixture comprising a crude-solvent package sample is taken with a disposable pipet and one liquid drop of the crude oil mixture is dropped onto a filter paper. The crude-solvent package sample spreads on the filter paper quickly and creates a circular area of darkened spot on the filter paper. If the liquid drop is a solution, the circular area will appear homogeneous, and the crude oil is soluble in the solvent package. If the liquid is a mixture, the circular area has different colors from the center to the edge, which typically comprises a center being darker than the lighter edges as shown in a) of FIG. 3. In this case, the crude oil is determined to be insoluble in the solvent package. Most of the color variations of the drop spreading may be easily identified with visible light, but there are times that visible light and/or UV light may be needed to identify the separation of the components of the crude oil mixture with conjugated π bonds (e.g., aromatics) as shown b) in FIG. 3. Through the methods disclosed herein, good or soluble solvent packages and bad or insoluble solvent packages for the crude oil may be determined and/or identified with ease and accuracy. The $\delta D$, $\delta P$, $\delta H$, and $R_0$ values may then be calculated and/or analyzed with the HSPiP software.

In one or more embodiments, the present methods disclosed herein may measure, determine, identify, and/or collect HSP information (i.e., $\delta D$, $\delta P$, $\delta H$, and $R_0$ values) for the production chemicals disclosed herein. The HSP information for the production chemicals may be calculated, predicted, and/or recorded via the methods disclosed herein. In an embodiment, the HSP information may be determined via one or more known processes reported within known literatures. In some embodiments, the production chemicals disclosed herein may be mixed with, combined with, added to, and/or included into at least one solvent package disclosed herein. Additionally, the at least one solvent package comprising the production chemicals may be added or applied to, incorporated or included into, and/or mixed or disposed within the crude oil to be treated with the one or more production chemicals.

In embodiments, a concentration of the one or more production chemicals within the at least one solvent package may be at least about 1 wt %, at least about 5 wt %, at least about 10 wt %, at least about 15 wt %, or at least about 20 wt %, wherein all weight percentages are calculated to the total weight of the at least one solvent package or a combination of the production chemical and the at least one solvent package. Additionally, the concentration of the production chemicals within the at least one solvent package may be less than about 50 wt %, less than about 40 wt %, less than about 30 wt %, less than about 25 wt %, or less than about 20 wt %, wherein all weight percentages are calculated to the total weight of the at least one solvent package or a combination of the production chemical and the at least one solvent package. In an embodiment, the concentration of the production chemicals within the at least one solvent package may be about 20 wt %, less than about 20 wt %, or more than about 20 wt %, wherein all weight percentages are calculated to the total weight of the at least one solvent package or a combination of the production chemical and the at least one solvent package A solubility observation of the production chemicals within the at least one solvent package may be performed at plurality of different temperatures as the solubility results vary at different temperature. In some embodiments, the solubility results for the production chemicals within the at least one solvent package are illustrated within Table 3. With respect to solubility results set forth in Table 3, the numeral "1" denotes that the production chemical is soluble in the solvent package, and "0" denotes that the production chemical is insoluble in the solvent package. Table 3 also includes example data recordings for the HSP information (i.e., $\delta D$, $\delta P$, and $\delta H$ values) of the solvent packages disclosed herein.

TABLE 3

| Solvent package | | | | Test temperatures (° C.) | | | | |
|---|---|---|---|---|---|---|---|---|
| ID | δD | δP | δH | 65 | 35 | 25 | 10 | 4 |
| HSP-1 | 14.9 | 0 | 0 | 1 | 1 | 1 | 1 | 0 |
| HSP-2 | 14.9 | 0.3 | 0.8 | 1 | 1 | 1 | 1 | 1 |
| HSP-3 | 15 | 0.5 | 0.4 | 1 | 1 | 1 | 1 | 0 |
| HSP-4 | 15 | 0.6 | 1.7 | 1 | 1 | 1 | 1 | 1 |
| HSP-5 | 15.1 | 1.3 | 3.5 | 1 | 1 | 1 | 1 | 0 |
| HSP-6 | 15.1 | 1.4 | 0.8 | 1 | 1 | 1 | 1 | 0 |
| HSP-7 | 15.2 | 2.2 | 1.2 | 1 | 1 | 1 | 1 | 0 |
| HSP-8 | 15.3 | 3.5 | 2 | 1 | 1 | 1 | 1 | 0 |
| HSP-9 | 15.4 | 4.6 | 5 | 1 | 0 | 0 | 0 | 0 |
| HSP-10 | 15.5 | 5 | 2.8 | 1 | 1 | 1 | 0 | 0 |
| HSP-11 | 15.8 | 7.1 | 4 | 1 | 0 | 0 | 0 | 0 |
| HSP-12 | 15.9 | 3.8 | 2.3 | 1 | 1 | 1 | 0 | 0 |
| HSP-13 | 15.9 | 5.3 | 3 | 1 | 1 | 1 | 0 | 0 |
| HSP-14 | 15.9 | 7.6 | 4.3 | 1 | 0 | 0 | 0 | 0 |
| HSP-15 | 16 | 0 | 0.1 | 1 | 1 | 1 | 1 | 0 |
| HSP-16 | 16 | 0.8 | 0.5 | 1 | 1 | 1 | 1 | 1 |
| HSP-17 | 16 | 1.5 | 0.9 | 1 | 1 | 1 | 1 | 0 |
| HSP-18 | 16 | 2.3 | 1.3 | 1 | 1 | 1 | 1 | 1 |
| HSP-19a | 16 | 3.1 | 3 | 1 | 1 | 1 | 1 | 1 |
| HSP-20 | 16 | 9 | 5.1 | 1 | 0 | 0 | 0 | 0 |
| HSP-21 | 16.5 | 1.4 | 1 | 1 | 1 | 1 | 1 | 1 |
| HSP-22 | 16.5 | 2 | 3 | 1 | 1 | 1 | 1 | 1 |
| HSP-23 | 16.5 | 4 | 3 | 1 | 1 | 1 | 1 | 0 |
| HSP-24 | 16.5 | 4.9 | 3 | 1 | 1 | 1 | 1 | 0 |
| HSP-25a | 16.5 | 5.1 | 4 | 1 | 1 | 1 | 0 | 0 |
| HSP-26 | 16.5 | 7 | 5 | 1 | 0 | 0 | 0 | 0 |
| HSP-27 | 16.7 | 3 | 4 | 1 | 1 | 1 | 1 | 0 |
| HSP-28 | 16.7 | 8.9 | 6.1 | 1 | 0 | 0 | 0 | 0 |
| HSP-29 | 17 | 5.3 | 3.2 | 1 | 1 | 1 | 0 | 0 |
| HSP-30a | 17 | 6 | 6 | 1 | 1 | 0 | 0 | 0 |
| HSP-31 | 17.1 | 0.5 | 1.8 | 1 | 1 | 1 | 1 | 1 |
| HSP-32 | 17.4 | 3.8 | 2.6 | 1 | 1 | 1 | 1 | 0 |
| HSP-33 | 17.4 | 7.5 | 4.6 | 1 | 0 | 0 | 0 | 0 |
| HSP-34 | 17.5 | 8.7 | 5.3 | 1 | 0 | 0 | 0 | 0 |
| HSP-35 | 17.6 | 0.5 | 1.1 | 1 | 1 | 1 | 1 | 0 |
| HSP-36 | 17.6 | 1.3 | 1.6 | 1 | 1 | 1 | 1 | 0 |
| HSP-37 | 17.7 | 1.2 | 3.6 | 1 | 1 | 1 | 1 | 1 |
| HSP-38 | 17.7 | 1.9 | 5.4 | 1 | 1 | 1 | 1 | 1 |
| HSP-39 | 17.8 | 0.7 | 1.7 | 1 | 1 | 1 | 1 | 0 |
| HSP-40 | 17.8 | 7.6 | 4.8 | 1 | 1 | 0 | 0 | 0 |
| HSP-41 | 17.8 | 8.4 | 5.1 | 1 | 0 | 0 | 0 | 0 |
| HSP-42 | 17.9 | 3 | 3 | 1 | 1 | 1 | 1 | 0 |
| HSP-43 | 17.9 | 3.5 | 2.9 | 1 | 1 | 1 | 0 | 0 |
| HSP-44 | 18 | 1.4 | 2 | 1 | 1 | 1 | 1 | 0 |
| HSP-45 | 18 | 1.8 | 2.2 | 1 | 1 | 1 | 1 | 0 |
| HSP-46 | 18 | 6 | 6 | 1 | 1 | 0 | 0 | 0 |

In one or more embodiments, the methods disclosed herein may measure, calculate, determine, collect, predict, or evaluate the HSP information (i.e., $\delta D$, $\delta P$, $\delta H$, and $R_0$ values) for the production chemicals. In some embodiments, the HSP values or information for the production chemicals disclosed herein may be calculated with trial-and-error by varying at least one of the coordinate of the center and the radius of the solubility spheres for the production products to maximize the fitting to the experimental observations. In some embodiments, the experimental observations may not be unique, or the experimental observations may fit within the center and/or the radius of the solubility sphere for the production products. In an embodiment, an average of eight (8) calculations may be reported for the production chemicals.

To obtain valid results for the HSP values or information of the production chemicals, one important or relevant factor to maximize may be the "Fit" value as shown in Table 4. If the calculation can completely fit the experimental results (i.e., all soluble solvents are inside the sphere of a production chemical, and all insoluble solvents are outside), then the "Fit" value is denoted as or assigned a "1" numeral. A "Fit" value of less than 0.9 may indicate the calculation of the HSP information for the production chemicals may not be reliable and the experiment results or solvent selection should be revisited. Since the calculations of the HSP information for the production chemicals are not unique, deviations between each calculation may also be inspected. In embodiments, a large standard deviation may indicate that there may be large variations in positioning the solubility sphere associated with a production chemical. As a result, one or more solvents may be necessary to refine the solubility results, and solubility experiments with at least one additional solvent should be performed. It may also be noted that the standard deviation for a very small value of $\delta P$ or $\delta H$ may be large or increased.

TABLE 4

| Temperature, | HSP values | | | | | Standard deviations | | | |
|---|---|---|---|---|---|---|---|---|---|
| °C. | $\delta D$ | $\delta P$ | $\delta H$ | $R_0$ | Fit | $\delta D$ | $\delta P$ | $\delta H$ | $R_0$ |
| 35 | 17.5 | 2.9 | 0.9 | 6.1 | 1.000 | 0.3% | 5.8% | 16.0% | 0.6% |
| 25 | 16.3 | 1.6 | 2.5 | 4.1 | 1.000 | 0.5% | 2.7% | 6.4% | 0.0% |
| 10 | 16.2 | 0.2 | 4.2 | 4.9 | 0.968 | 0.5% | 4.6% | 0.6% | 0.0% |

In one or more embodiments, the methods disclosed herein may correlate at least two production chemicals based on the HSP information (i.e., at least $\delta D$, $\delta P$, and $\delta H$ values) of the at least two production chemicals. Additionally, the methods disclosed herein may correlate at least two crude oils and/or at least two production chemicals based on HSP information of the at least two crude oils and/or the at least two production chemicals. For example, the methods disclosed herein may correlate production chemical performances of at least two production chemicals based on the HSP information (i.e., at least $\delta D$, $\delta P$, and $\delta H$ values) of the at least two production chemicals.

As set forth above, a functioning production chemical in a crude oil may have one or more functional segments of the production chemical molecule that may be fully extended in the crude oil environment of the crude oil under the functioning conditions. In some embodiments, a production chemical that is fully extended in a crude oil should be soluble or is readily soluble in the crude oil. Based on the HSP theory, the $\delta D$, $\delta P$, and $\delta H$ values of the production chemical should be close to, adjacent to, or abutting the $\delta D$, $\delta P$, and $\delta H$ values of the crude oil in the solubility space associated with the production chemical and/or the crude oil. In addition, the point of the production chemical defined by $\delta D$, $\delta P$, and $\delta H$ values should be or may be positioned near, adjacent, or within and/or abutting the solubility sphere of the crude oil. In an embodiment, the pour point depressing performances of several production chemicals in at least two different crude oils may demonstrate one or more relationships between at least one production chemicals and at least one crude oil.

In one or more embodiments, the HSP information values (i.e., $\delta D$, $\delta P$, $\delta H$, and $R_0$ values) for two crude oils were measured and reported in Table 5. It is noted that the HSP information for the crude oils did not vary significantly with temperature in the studied range of about 10-65° C., so the same HSP information may be used for all temperatures. From the HSP information of the two crudes, the $\delta D$ values of the two crudes may be similar or substantially similar values, but the $\delta P$ and $\delta H$ values of the two crudes may differ by about a few folds. It is believed that a higher water content (existing as emulsion) of Crude oil 2 could have contributed to the differences between the HSP information of Crude 1 and Crude 2 set forth in Table 5.

TABLE 5

| HSP values | $\delta D$ | $\delta P$ | $\delta H$ | $R_0$ |
|---|---|---|---|---|
| Crude 1 | 16.5 | 0.11 | 1.41 | 3.65 |
| Crude 2 | 16.02 | 0.98 | 3.49 | 3.94 |

In one or more embodiments, the production chemicals disclosed herein may be added or applied to one or more crude oils to change, alter, or modify one or more physical properties of the one or more crude oils. For example, the production chemicals disclosed herein may be or may comprise at least one pour point depressant and/or may depress one or more pour points associated with the one or more crude oils. In an embodiment, the production chemicals herein may comprise twenty-one (21) pour point depressants (hereinafter "PPDs") of four (4) different chemistries that were screened for a crude oil, such as, for example, Crude oil 1. The effectiveness of the production chemicals disclosed herein as PPDs are listed in the pour point column in Table 6.

A majority of the crude oils may have a pour point around about 30-35° C. and/or the PPDs need to be in solution above but close or adjacent to wax crystallization temperatures in order to function as PPDs. Therefore, the HSP information at 35° C. may be utilized to perform, calculate, or determine one or more correlation exercises. All PPDs with measured HSP values at 35° C. are also listed in the Table 6 along with associated standard deviations and "Fit" values. Two distances were evaluated for the correlation. The ordinary distances between the PPDs and the crude oil are plottable as normal 3D Cartesian coordinates, and the Hansen space distance from the literature may emphasize or put more weight on the dispersive interactions. The ordinary distances $D_a$ may be calculated with Equation 1.

$$\text{Distance} \equiv D_a = \sqrt{(\delta D_{PPD} - \delta D_{crude})^2 + (\delta P_{PPD} - \delta P_{crude})^2 + (\delta H_{PPD} - \delta H_{crude})^2} \quad \text{Equation 1}$$

The Hansen space distance between PPD and crude oil, $R_a$, may be defined with Equation 2.

$$R_a = \sqrt{4(\delta D_{PPD} - \delta D_{crude})^2 + (\delta P_{PPD} - \delta P_{crude})^2 + (\delta H_{PPD} - \delta H_{crude})^2} \quad \text{Equation 2}$$

For comparisons to determine which parameter may give or provide a better correlation between HSP information values and performances, both ordinary distances in 3D space and Hansen space distances were calculated and listed in Table 6. It was found that the ordinary distances may have one or more better correlations. Therefore, only said correlation will be further discussed in the present disclosure. However, the present disclosure is not limited to only said correlation and also includes the Hansen distance Ra values. For example, the Hansen distance Ra value may provide or achieve a better or improved correlation than the true distance in some embodiments.

TABLE 6

| ID | Chemistry | HSP info | | | | standard deviations | | | | Fit | Pour point, °C. | Distance | $R_a$ |
|---|---|---|---|---|---|---|---|---|---|---|---|---|---|
| | | δD | δP | δH | $R_0$ | δD | δP | δH | $R_0$ | | | | |
| Crude oil 1 | | 16.5 | 0.11 | 1.41 | 3.65 | 0.6% | 27.8% | 14.3% | 2.1% | 0.993 | 35 | NA | NA |
| 1 | EVA | 17.56 | 2.53 | 0.14 | 6.93 | 0.2% | 5.9% | 75.3% | 2.0% | 1.000 | 34 | 2.93 | 3.46 |
| 2 | EVA | 17.40 | 2.25 | 4.59 | 7.2 | 0.0% | 0.0% | 0.0% | 0.0% | 1.000 | 34 | 3.94 | 4.23 |
| 3 | EVA | 19.19 | 0.33 | 2.32 | 8.9 | 0.6% | 39.6% | 18.5% | 3.2% | 0.997 | 33 | 2.85 | 5.46 |
| 4 | EVA | 18.84 | 2.13 | 0.25 | 8.69 | 0.4% | 3.6% | 28.4% | 1.3% | 0.980 | 33 | 3.30 | 5.23 |
| 5 | EVA | 19.08 | 0.47 | 1.92 | 8.95 | 1.2% | 87.9% | 23.2% | 4.5% | 0.996 | 32 | 2.65 | 5.20 |
| 6 | EVA | 19.04 | 0.52 | 1.91 | 8.89 | 1.1% | 98.5% | 26.1% | 5.8% | 0.996 | 31 | 2.62 | 5.12 |
| 7 | EVA | 18.13 | 0.11 | 3.72 | 7.59 | 0.5% | 79.5% | 3.6% | 0.5% | 0.991 | 29 | 2.83 | 4.00 |
| 8 | EVA | 17.51 | 2.65 | 1.17 | 6 | 0.1% | 3.2% | 5.7% | 0.0% | 1.000 | 29 | 2.74 | 3.25 |
| 9 | EVA | 17.51 | 2.19 | 1.62 | 5.91 | 0.1% | 5.0% | 6.2% | 0.6% | 1.000 | 29 | 2.32 | 2.91 |
| 10 | EVA | 18.24 | 0.17 | 2.73 | 7.13 | 0.7% | 27.8% | 6.3% | 2.2% | 0.883 | 28 | 2.18 | 3.72 |
| 11 | EVA | 17.71 | 0.86 | 1.77 | 3.8 | 0.2% | 8.5% | 5.2% | 0.0% | 0.983 | 26 | 1.47 | 2.56 |
| 12 | OMAC | 16.14 | 3.85 | 2.23 | 5.1 | 0.00% | 0.00% | 0.00% | 0.00% | 1.000 | 35 | 3.85 | 3.90 |
| 13 | OMAC | 17.17 | 3.42 | 0.15 | 6.39 | 0.50% | 4.50% | 56.10% | 1.60% | 0.990 | 34 | 3.60 | 3.79 |
| 14 | OMAC | 17.55 | 2.55 | 0.15 | 6.88 | 0.4% | 6.9% | 88.3% | 2.2% | 1.000 | 30 | 2.94 | 3.46 |
| 15 | OMAC | 17.18 | 2.94 | 1.16 | 5.75 | 0.10% | 1.70% | 3.80% | 0.90% | 1.000 | 29.5 | 2.92 | 3.15 |
| 16 | OMAC | 17.18 | 2.93 | 1.13 | 5.78 | 0.10% | 0.50% | 4.60% | 0.80% | 1.000 | 29 | 2.91 | 3.14 |
| 17 | PAA | 17.45 | 3.15 | 0.72 | 6.05 | 0.40% | 1.90% | 14.20% | 0.90% | 1.000 | 35 | 3.26 | 3.65 |
| 18 | PAA | 17.21 | 3.20 | 0.73 | 5.8 | 0.20% | 4.40% | 18.20% | 0.00% | 1.000 | 30 | 3.24 | 3.47 |
| 19 | SMA | 19.82 | 0.55 | 0.45 | 9.94 | 0.60% | 45.90% | 86.90% | 3.20% | 0.976 | 34 | 3.48 | 6.72 |
| 20 | SMA | 17.54 | 2.92 | 0.93 | 6.11 | 0.30% | 5.80% | 16.00% | 0.60% | 1.000 | 32 | 3.03 | 3.53 |
| 21 | SMA | 17.44 | 2.29 | 0.92 | 6.19 | 2.90% | 12.40% | 79.80% | 14.00% | 0.992 | 30 | 2.42 | 2.92 |

Figure 4:
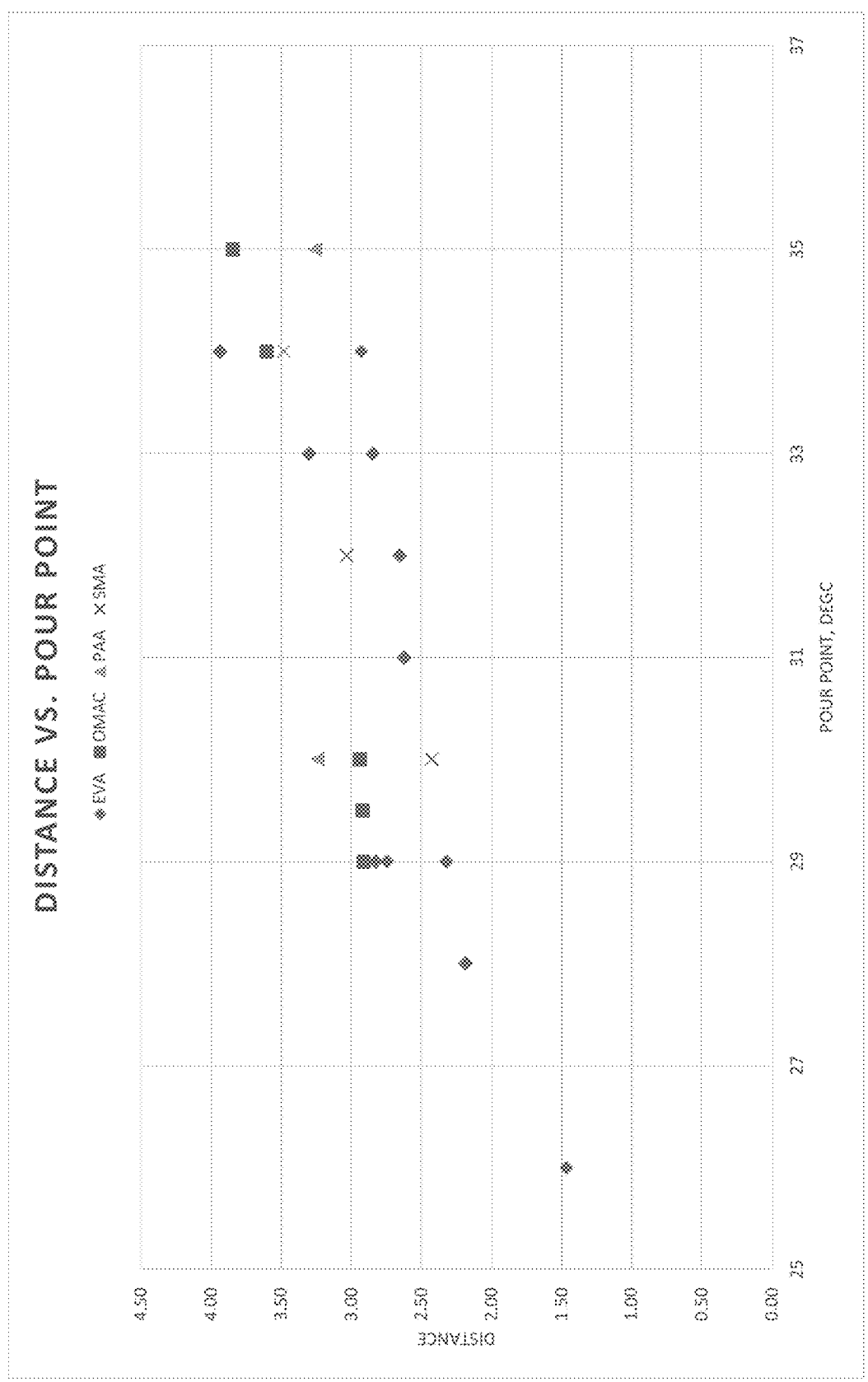
FIG. 4 illustrates a graph correlating pour point with the distance between pour point depressant (hereinafter "PPD") and a first crude oil 1 with HSP values at 35° C., according to one or more examples of the disclosure.

In one or more embodiments, distances between PPDs and crude oils may be correlated and/or plottable to further illustrate said correlation. For example, the results of the HSP distances versus Crude oil 1 pour points are plotted in FIG. 4. It is visible that there is a positive correlation between the pour point and the distance between PPD and the crude oil (i.e., the further the distance, then the higher the pour point of the oil). It is understandable that different chemistry of the PPD may require different HSP distances to perform, the different chemistries results are plotted as different traces in FIG. 4.

Figure 5:
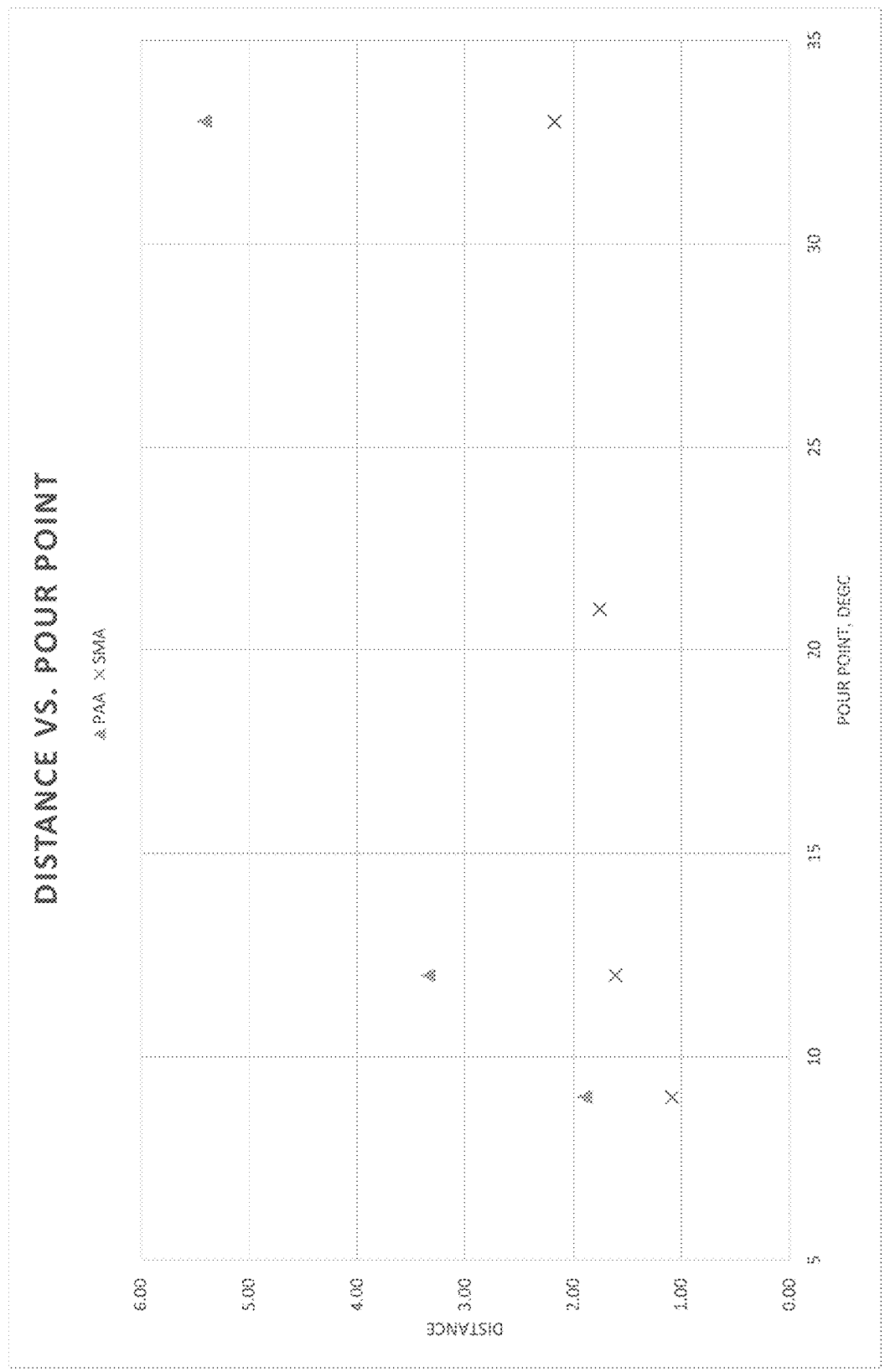
FIG. 5 illustrates a graph correlating pour point with the distance between PPD and a second crude oil 2 with HSP values at 10° C., according to one or more examples of the disclosure.

Similarly, the correlation attempts for Crude oil 2 with PPDs of two different chemistries are given in Table 7 and illustrated in FIG. 5. In this crude oil, most of the crude pour points are about ~10° C.; therefore, 10° C. HSP values are used for the correlations. From FIG. 5, it may be clear that a similar trend also exists with better performances coming from the PPDs with less distances to that of Crude oil 2.

utilize the HSP approach to select at least one production chemical. For example, performances of the PPDs may be correlated to the HSP distances between the production chemical and the crude oil being treated by the production chemical, and the correlation(s) may be utilized to improve a PPD selection. The methods disclosed herein may identify, select, and/or predict at least one production chemical that is efficient for treating the crude oil. For example, performance tests may be utilized to screen through dozens of PPDs with a specific crude oil to find at least one performing production chemical for treating the specific crude oil, but the performance tests may be labor intensive, time consuming, and/or crude oil consuming. However, the methods disclosed herein may greatly simplify identification, selection, and/or prediction of one or more production chemicals for treating crude oils. For example, HSP values or information for the production chemicals may be measured regardless of a

TABLE 7

| ID | Chem. | HSP info | | | | standard deviations | | | | Fit | Pour point, °C. | Distance | $R_a$ |
|---|---|---|---|---|---|---|---|---|---|---|---|---|---|
| | | δD | δP | δH | $R_0$ | δD | δP | δH | $R_0$ | | | | |
| Crude oil 2 | NA | 16.0 | 1.0 | 3.5 | 3.9 | 1.4% | 31.7% | 7.6% | 3.5% | 0.979 | NA | NA | NA |
| 22 | PAA | 16.8 | 5.1 | 0.1 | 6.4 | 0.5% | 1.8% | 76.8% | 0.8% | 0.999 | 33 | 5.41 | 5.55 |
| 18 | PAA | 16.2 | 1.6 | 0.2 | 3.1 | 0.7% | 6.3% | 66.7% | 1.1% | 0.962 | 12 | 3.34 | 3.35 |
| 17 | PAA | 16.8 | 0.1 | 2.0 | 4.1 | 0.6% | 107.5% | 8.4% | 0.0% | 0.844 | 9 | 1.89 | 2.32 |
| 23 | SMA | 16.9 | 0.1 | 1.7 | 4.3 | 0.4% | 35.7% | 8.7% | 1.9% | 0.976 | 33 | 2.18 | 2.69 |
| 24 | SMA | 16.6 | 0.1 | 2.1 | 4.4 | 0.7% | 38.2% | 9.5% | 0.8% | 0.986 | 21 | 1.76 | 2.00 |
| 19 | SMA | 16.6 | 0.1 | 2.3 | 4.2 | 0.5% | 32.6% | 4.3% | 0.0% | 0.995 | 12 | 1.61 | 1.91 |
| 20 | SMA | 16.2 | 0.2 | 4.2 | 4.9 | 0.5% | 4.6% | 0.6% | 0.0% | 0.968 | 9 | 1.09 | 1.15 |

In one or more embodiments, the methods disclosed wherein may select one or more production chemicals based on the HSP values or information of the one or more production chemicals and/or one or more crude oils. In some embodiments, the present methods disclosed herein may specific crude oil to be treated by the production chemicals via the methods disclosed herein.

The methods disclosed herein may establish, generate, produce, and/or provide at least one database (hereinafter "the database") that comprises the HSP information of one or more production chemicals. In some embodiments, the database may be a properties database or dataset comprising property information of the one or more production chemicals. When a new, different, or subsequent crude oil (hereinafter "new crude oil") needs or requires treatment, HSP information of the new crude oil may be measured, determined, and/or identified for comparing with the HSP information of the production chemicals set forth in the database. The methods disclosed herein may compare the HSP information of the production chemicals and the HSP information of the new crude oil to determine, identify, and/or measure at least one correlation between the HSP information of at least one production chemical and the new crude oil. The correlation determined by the method disclosed herein may represent or identify the at least one production chemical that is or may be suitable for subsequently treating the new crude oil. For example, the present methods disclosed herein may select a plurality of production chemicals or at least one production chemical from the database that has a small or substantially small HSP distance to new crude oil, then the methods may perform one or more confirmational tests to determine a best performing production chemical from the selected plurality of production chemicals. In an embodiment, the present methods disclosed herein may select at least one chemistry of the production chemical(s) that may be effective for the new crude oil based on past treatment experiences, and then the methods may narrow down the chemical product selection with the HSP distance calculation as disclosed herein. As a result, the chemical selection efficiency can be greatly improved with the HSP approach utilized by the present methods disclosed herein.

In at least one embodiment, the methods disclosed herein may select at least one best performing production chemical via more than one of the following steps. The steps of the methods disclosed herein may be performed or executed consecutively or substantially consecutively and/or the methods steps may comprise one or more computer-implemented method steps. In some embodiments, at least two of the method steps disclosed herein may be performed or executed at the same time, substantially the same time, instantaneously, or immediately after each other. For example, the methods disclosed herein may comprises one or more computer-implemented steps that may be performed or executed by at least one computer software application.

For example, at least one method disclosed herein for picking, selecting, or determining a best qualified production product from a plurality of qualified production products may comprise a step of measuring or collecting HSP values or information of a target crude oil and calculating HSP distance values between all production products and the target crude oil based on the existing HSP values or information for all production products that may be available and/or accessible via an existing HSP production products database. Further, the methods disclosed herein may comprise steps of selecting production products having a calculated HSP distance value that is less than one (i.e., value<1) and select at least two chemistries (i.e., three chemistries) of the production products based on historical data of similar crude oil (i.e., at least one similar field, at least one similar region, at least one similar formation, at least one combination thereof, or the like). In embodiments, the historical data may be available and/or accessible via at least one database or dataset associated with the methods disclosed herein. Still further, the methods disclosed herein may comprise selecting qualified production products based on at least one operation condition, the selected production products, and/or the selected at least two chemistries of the production products. In embodiments, the at least one operation condition may comprise at least one selected from additive pump acceptable pump rates, deep water stabilities, flammabilities, local availabilities, cost targets, and combinations thereof. The additive pump acceptable pump rate may define a concentration requirement of the production product or production chemical package, and the deep water stability may be based on whether the selected production product or production chemical package pass one or more deep-water qualification tests focusing on low temperature package stability. If the operation condition requires non-flammable product packages, the method may eliminate or deselect production products and/or product packages that are flammable. Regarding local availability, production products and/or product packages that are not locally available may be eliminated or deselected by the methods disclosed herein. Still further, the methods disclosed herein may comprise, within each chemistry of the qualified products, a step of further selecting or narrowing the selected production products to a number of candidate production products based on at least one of the difference between $R_a$ values, the difference between $D_a$ values, or a combination thereof. For example, the number of candidate production products may be three (3) candidate products that may be selected from or determined by selecting the three (3) candidate products having the smallest differences between $R_a$ values, the closest differences between $D_a$ values, or a combination thereof. Please note that the two selection criteria (i.e., $R_a$ and $D_a$) may not yield the same candidate production products and the final selection of the candidate production products may be based on performance validation tests of the candidate production products. Moreover, the methods disclosed herein may comprises a step of performing performance tests with respect to the candidate production products to validate the selected candidate production products. Furthermore, the methods disclosed herein may comprise a step of selecting best qualified production product from the candidate production products based on the two selection criteria, the performance tests, or a combination thereof.

In one or more embodiments, the methods disclosed herein may utilize production chemistry to determine one or more other HSP applications for the production chemicals based on the HSP information set forth in the database and/or dataset. For example, the methods disclosed herein may select one or more production chemicals based on the HSP information associated with one or more performances of the one or more production chemicals. In some embodiments, one or more additional applications may be built on or designed are the HSP information that may be gathered by the methods disclosed herein. For example, knowing the HSP information and/or values of at least one chemical may allow the methods disclosed herein to select one or more different combinations of one or more solvents for formulating a product package. As a result, the methods disclosed herein may formulate a production package comprising at least one chemical, at least one solvent, and/or one or more combinations of one or more solvents based on the HSP information set forth in the database. This is especially effective when formulating product packages for low temperature stability in applications like Deepwater environment. Solubility of chemicals usually decreases as temperature decreases; therefore, it is pickier to select the right solvent package to ensure a stable product package. From the collected HSP information (e.g., Table 4), in addition to the reduction of the interaction sphere radium, it is also evident that the center of the sphere could change which may demand a solvent package for low temperature be very different from that of room or higher temperature. With HSP information and/or values as set forth in the database, the methods disclosed herein may select at least one solvent package which may target or satisfy one specific properties of a crude oil. For example, the methods disclosed herein may select at least one solvent package based on one or more production chemical application requirements, such as, for example, but not limited to, a low temperature stability, a high flash point, at least one environmental factor, at least one combination thereof, and/or the like.

Examples in the present disclosure, such as, the methods disclosed herein may also be directed to, included and/or incorporated into or implemented via at least one non-transitory computer-readable medium storing computer-executable instructions and executable by one or more processors of at least one computer via which the computer-readable medium is accessed. The computer-executable instructions may comprise the present methods disclosed herein or at least one or more steps of or associated with the present methods disclosed herein. In some embodiments, the non-transitory computer-readable medium and/or the computer-executable instructions may comprise the present database disclosed herein. Moreover, the HSP information and/or values for the one or more chemicals and/or the one or more crude oils may be accessible via one or more of the methods, database(s), dataset(s), non-transitory computer-readable medium, and/or the computer-executable instructions disclosed herein. In embodiments, the database(s) and/or the dataset(s) disclosed herein may comprise a plurality of databases and/or a plurality of datasets, wherein the pluralities of databases and/or the datasets comprise at least the HSP information and/or values for the one or more chemicals.

A computer-readable media may be any available media that may be accessed by a computer. By way of example, such computer-readable media may comprise RAM, ROM, EEPROM, CD-ROM or other optical disk storage, magnetic disk storage or other magnetic storage devices, or any other medium that may be used to carry or store desired program code in the form of instructions or data structures and that may be accessed by a computer or computing device. Disk and disc, as used herein, includes compact disc (CD), laser disc, optical disc, digital versatile disc (DVD), floppy disk and Blu-ray® disc where disks usually reproduce data magnetically, while discs reproduce data optically with lasers.

Moreover, the methods disclosed herein may be included and/or incorporated into or may be implemented via one or more software applications. Note also that the software implemented aspects of the subject matter disclosed herein may be encoded on some form of program storage medium or implemented over some type of transmission medium. The program storage medium is a non-transitory medium and may be magnetic (e.g., a floppy disk or a hard drive) or optical (e.g., a compact disk read only memory, or "CD ROM"), and may be read only or random access. Similarly, the transmission medium may be twisted wire pairs, coaxial cable, optical fiber, or some other suitable transmission medium known to the art. The subject matter disclosed herein is not limited by these aspects of any given implementation.

The foregoing description, for purposes of explanation, used specific nomenclature to provide a thorough understanding of the disclosure. However, it will be apparent to one skilled in the art that the specific details are not required in order to practice the systems and methods described herein. The foregoing descriptions of specific examples are presented for purposes of illustration and description. They are not intended to be exhaustive of or to limit this disclosure to the precise forms described. Obviously, many modifications and variations are possible in view of the above teachings. The examples are shown and described in order to best explain the principles of this disclosure and practical applications, to thereby enable others skilled in the art to best utilize this disclosure and various examples with various modifications as are suited to the particular use contemplated. It is intended that the scope of this disclosure be defined by the claims and their equivalents below.

What is claimed is:

1. A method for selecting one or more production chemicals for a crude oil application, the method comprising:
   measuring Hansen Solubility Parameters (HSP) values for a plurality of production chemicals to generate HSP information of the plurality of production chemicals;
   generating a plurality of production chemical packages, each production chemical package of the plurality of production chemical packages including a set of multiple production chemicals of the plurality of production chemicals;
   measuring, for each of the plurality of production chemical packages, a plurality of HSP values at a plurality of different temperatures to generate HSP information of the plurality of production chemical packages, wherein the plurality of different temperatures correspond to a plurality of pour points of a plurality of crude oils;
   measuring HSP values for the plurality of crude oils to generate HSP information of the plurality of crude oils, wherein the HSP values comprise a strengths of dispersion interaction $\delta D$ value, a polar interaction $\delta P$ value, a hydrogen bonding $\delta H$ value, and a solubilizing power $R_0$ value;
   selecting a first production chemical package of the plurality of production chemical packages;
   comparing the HSP information of the first production chemical package to the HSP information of a target crude oil of the plurality of crude oils;
   when (i) the HSP information of a production chemical or the HSP information of a combination of production chemicals, of the first production chemical package, (ii) and the HSP information of the target crude oil satisfy a criteria, selecting the production chemical or the combination of production chemicals, wherein the selected production chemical or the selected combination of production chemicals has HSP values within a radius of a 3D sphere on a 3D graph, and wherein the HSP values for the target crude oil are located at a center of the 3D sphere;
   inhibiting at least one of: corrosion, emulsion, gas hydrates, scale, bacteria, foam, wax, paraffin, asphaltenes, grease build-up, heterogeneous material build-up, or hydrogen sulfide within the target crude oil by adding the selected production chemical or the selected combination of production chemicals to the target crude oil, a production stream associated with the target crude oil, equipment associated with the target crude oil, or a combination thereof.

2. The method of claim 1, further comprising measuring the HSP values of the target crude oil by utilizing chromatography filter paper before comparing the HSP information of the first production chemical package to the HSP information of the target crude oil.

3. The method of claim 1, wherein the selected production chemical or the selected combination of production chemicals is at least one chemical selected from a group consisting of biocides, corrosion inhibitors, de-foamers, emulsifiers, foamers, rig washes, scale inhibitors, hydrogen sulphide scavengers, formulated emulsion breakers, paraffin inhibitors, gas hydrate inhibitor, asphaltene inhibitor, de-oilers/water clarifiers, and at least one combination thereof.

4. A method comprising:
   measuring, for each of a plurality of production chemical packages, Hansen Solubility Parameters (HSP) values at plurality of different temperatures to generate HSP information of the plurality of production chemical packages, wherein the plurality of different temperatures correspond to a plurality of pour points of a plurality of crude oils, and wherein each production chemical package includes a set of multiple production chemicals;
   measuring HSP values for the plurality of crude oils to generate HSP information of the plurality of crude oils, wherein the HSP values comprise a strengths of dispersion interaction $\delta D$ value, a polar interaction $\delta P$ value, a hydrogen bonding $\delta H$ value, and a solubilizing power $R_0$ value;
   predicting chemical performances of using the plurality of production chemical packages to treat the plurality of crude oils by correlating the HSP information of the plurality of production chemical packages and the HSP information of the plurality of crude oils;
   selecting, based on the predicted chemical performances, for treating a target crude oil of the plurality of crudes oils, at least one production chemical, of the multiple production chemicals, wherein the selected production chemical has HSP values within a radius of a 3D sphere on a 3D graph, and wherein the HSP values for the target crude oil are located at center of the 3D sphere; and
   inhibiting at least one of: corrosion, emulsion, gas hydrates, scale, bacteria, foam, wax, paraffin, asphaltenes, grease build-up, heterogeneous material build-up, or hydrogen sulfide within the target crude oil by adding the selected at least one production chemical or combination of production chemicals to the target crude oil, a production stream associated with the target crude oil, equipment associated with the target crude oil, or a combination thereof.

5. The method of claim 4, wherein the selected at least one production chemical is at least one chemical selected from a group consisting of biocides, corrosion inhibitors, de-foamers, emulsifiers, foamers, rig washes, scale inhibitors, hydrogen sulphide scavengers, formulated emulsion breakers, paraffin inhibitors, gas hydrate inhibitor, asphaltene inhibitor, de-oilers/water clarifiers, and at least one combination thereof.

6. A method for selecting one or more production chemicals for a crude oil application, the method comprising:
   measuring, for each solvent package of a plurality of solvent packages, Hansen Solubility Parameters (HSP) values at plurality of different temperatures, each solvent package comprising a combination of solvents, wherein the plurality of different temperatures correspond to a plurality of pour points of a plurality of crude oils, wherein the plurality of solvent packages covers a Hansen space of a target crude oil, and wherein the Hansen space comprises a 3D spherical graph with a dispersion interaction SD HSP value, a polar interaction $\delta P$ HSP value, and a hydrogen bonding $\delta H$ HSP value, of the target crude oil, at a center of the 3D spherical graph, and wherein a radius of the 3D spherical graph is a solubilizing power $R_0$ value of the target crude oil;
   selecting at least one solvent package for the crude oil application in response to measured HSP values of the at least one solvent package being located with the 3D spherical graph of the target crude oil; and
   inhibiting at least one of: corrosion, emulsion, gas hydrates, scale, bacteria, foam, wax, paraffin, asphaltenes, grease build-up, heterogeneous material build-up, or hydrogen sulfide within the target crude oil by adding the selected at least one solvent package to the target crude oil, a production stream associated with the target crude oil, equipment associated with the target crude oil, or a combination thereof.

7. The method of claim 6, wherein the selected at least one solvent package comprises at least one chemical selected from a group consisting of biocides, corrosion inhibitors, de-foamers, emulsifiers, foamers, rig washes, scale inhibitors, hydrogen sulphide scavengers, formulated emulsion breakers, paraffin inhibitors, gas hydrate inhibitor, asphaltene inhibitor, de-oilers/water clarifiers, and at least one combination thereof.

* * * * *